United States Patent [19]

Butler et al.

[11] Patent Number: 4,563,469

[45] Date of Patent: Jan. 7, 1986

[54] DERIVATIVES OF N-[2-(TETRAHYDRO-3,5-DIOXO-1H-PYRROLIZIN-7A(5H)-YL)ETHYL]AMINE AS COGNITION ACTIVATORS

[75] Inventors: Donald E. Butler; James D. Leonard, both of Ann Arbor, Mich.

[73] Assignee: Warner-Lambert Company, Morris Plains, N.J.

[21] Appl. No.: 632,917

[22] Filed: Jul. 20, 1984

[51] Int. Cl.[4] .................. A61K 31/40; A61K 31/445; C07D 401/12; C07D 487/08
[52] U.S. Cl. .................................. 514/339; 514/413; 546/272; 548/453
[58] Field of Search .................. 548/453; 546/272; 514/339, 413

[56] References Cited

FOREIGN PATENT DOCUMENTS 0095345 11/1983 European Pat. Off. ............ 548/453

OTHER PUBLICATIONS

Noller, Chemistry of Organic Compounds, 3rd ed., (1965), p. 339.
Sorm, et al., C.A. 49:292c, (1955).

*Primary Examiner*—Joseph Paul Brust
*Attorney, Agent, or Firm*—Jerry F. Janssen

[57] ABSTRACT

Novel derivatives of N-[2-(tetrahydro-3,5-dioxo-1H-pyrrolizin-7a(5H)-yl)ethyl]amine are effective as cognition activators for reversing the effects of electroshock induced amnesia. A method of preparing the compounds, a useful intermediate in their preparation, pharmaceutical compositions, and a method of treatment are also disclosed.

28 Claims, No Drawings

DERIVATIVES OF N-[2-(TETRAHYDRO-3,5-DIOXO-1H-PYRROLIZIN-7A(5H)-YL)ETHYL]AMINE AS COGNITION ACTIVATORS

BACKGROUND OF THE INVENTION

This invention relates to compounds and pharmaceutical compositions useful for reversing the effects of electroconvulsive shock-induced amnesia, a method of preparing the compounds, and of reversing amnesia. More particularly, this invention is concerned with certain derivatives of N-[2(tetrahydro-3,5-dioxo-1H-pyrrolizin-7a(5H)-yl)ethyl]amine having pharmacological activity for reversing the effects of electroconvulsive shock-induced amnesia, pharmaceutical compositions including these compounds, a method of preparing the compounds, and of reversing the effects of induced amnesia.

The ethyl ester of tetrahydro-3,5-dioxo-1H-pyrrolizin-7a(5H)-propanoic acid has been synthesized as a chemical intermediate as disclosed in *Chem. Listy.* 47:1359–1365 (1953); (*Coll. Czech. Chem. Comm*, 19:298 (1954) in English); (*Chem. Abstr.* 49:292c (1955)).

SUMMARY OF INVENTION

In its broadest aspect, compounds in accordance with the present invention possess formula I

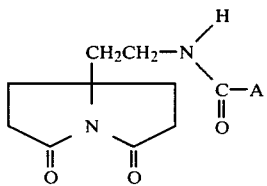

wherein A is $NR_1R_2$ where $R_1$ and $R_2$ are independently hydrogen, lower alkyl, or lower alkylene; wherein A is $NHR_3$ where $R_3$ is phenyl, phenylmethyl, N,N-bis(1methylethyl)aminoethyl or 4-pyridyl; or wherein A is $-OR_4$ where $R_4$ is lower alkyl, phenyl, phenylmethyl, or phenyl or phenylmethyl substituted in the 2-, 3-, or 4-position with chlorine, fluorine, lower alkoxy, or phenylmethoxy.

In one subgeneric aspect, compounds of the present invention possess structural formula I wherein A is $NR_1R_2$ and $R_1$ and $R_2$ are independently hydrogen, lower alkyl or lower alkylene.

In another subgeneric aspect, compounds of the present invention possess structural formula I wherein A is $NHR_3$ where $R_3$ is phenyl, phenylmethyl, N,N-bis-(1-methylethyl)aminoethyl or 4-pyridyl.

In a further subgeneric aspect, compounds of the present invention possess structural formula I where A is $-OR_4$ where $R_4$ is lower alkyl.

In another subgeneric aspect, compounds of the present invention possess structural formula I where A is $-OR_4$ where $R_4$ is phenyl or phenyl substituted in the 2-, 3-, or 4-position with chlorine, fluorine, lower alkoxy, or phenylmethoxy.

In another subgeneric aspect, compounds of the present invention possess structural formula I where A is $-OR_4$ where $R_4$ is phenylmethyl or phenylmethyl substituted in the 2-, 3-, or 4-position with chlorine, fluorine, lower alkoxy, or phenylmethoxy.

In another aspect of the present invention there are provided pharmaceutical compositions for reversing the effects of electroconvulsive shock-induced amnesia comprising a pharmaceutically effective amount of a compound having structural formula I as defined above, in combination with a pharmaceutically acceptable carrier.

DETAILED DESCRIPTION

As used throughout this specification and the appended claims, the term "lower alkyl" is meant to encompass groups derived by removal of one hydrogen atom from branched or unbranched saturated hydrocarbons of from one to six carbon atoms.

The term "lower alkoxy" is meant to encompass groups of the structure —OR where R is lower alkyl as previously defined.

The term "lower alkylene" is meant to encompass groups derived by removal of one hydrogen atom from branched or unbranched hydrocarbons of two to six carbon atoms containing at lest one carbon-carbon double bond.

The compounds of the present invention are capable of existing both in solvated and unsolvated forms including hydrates. In general, the forms solvated with such pharmaceutically acceptable solvents as water, ethanol, and the like are equivalent to the unsolvated forms for the purposes of the present invention.

Examples of compounds falling within the scope of the present invention include, but are not necessarily limited to the following:

N-[2-(tetrahydro-3,5-dioxo-1H-pyrrolizin-7a(5H)-yl-ethyl]urea;

N-methyl-N'-[2-[2-(tetrahydro-3,5-dioxo-1H-pyrrolizin-7a(5H)-yl)-ethyl]urea;

N-2-propenyl-N'-[2-(tetrahydro-3,5-dioxo-1H-pyrrolizin-7a(5H)-yl)-ethyl]urea;

N,N-dimethyl-N'-[2-(tetrahydro-3,5-dioxo-1H-pyrrolizin-7a(5H-yl)-ethyl]urea;

N,N-diethyl-N'-[2-(tetrahydro-3,5-dioxo-1H-pyrrolizin-7a(5H)-yl)-ethyl]urea;

N-phenyl-N'-[2-( tetrahydro-3,5-dioxo-1H-pyrrolizin-7a(5H)-yl-ethyl-]urea;

N-phenylmethyl-N'-[2-tetrahydro-3,5-dioxo-1H-pyrrolizin-7a(5H)-yl-)-ethyl]urea;

N-[2-[bis( 1-methylethyl)amino]ethyl]-N'-[2-tetrahydro-3,5-dioxo-1H-pyrrolizin-7a(5H)-yl-ethyl]urea;

N-4-pyridyl-N'-[2-(tetrahydro-3,5-dioxo-1H-pyrrolizin-7a(5H)-yl)-ethyl]urea;

[2-(tetrahydro-3,5-dioxo-1H-pyrrolizin-7a(5H)-yl)-ethyl]carbamic acid, methyl ester;

[2-(tetrahydro-3,5-dioxo-1H-pyrrolizin-7a(5H)-yl)-ethyl-carbamic acid, ethyl ester;

[2-tetrahydro-3,5-dioxo-1H-pyrrolizin-7a(5H)-yl-ethyl]-carbamic acid, phenyl ester;

[2-(tetrahydro-3,5-dioxo-1H-pyrrolizin-7a(5H)-yl)-ethyl]carbamic acid, 4-fluorophenyl ester;

[2-(tetrahydro-3,5-dioxo-1H-pyrrolizin-7a(5H)-yl)-ethyl]carbamic acid, 2-chlorophenyl ester;

[2-(tetrahydro-3,5-dioxo-1H-pyrrolizin-7a(5H)-yl)-ethyl-carbamic acid, 4-methoxyphenyl ester;

[2-(tetrahydro-3,5-dioxo-1H-pyrrolizin-7a(5H)-yl-ethyl]carbamic acid, phenylmethyl ester;

[2-(tetrahydro-3,5-dioxo-1H-pyrrolizin-7a(5H)-yl-ethyl]carbamic acid, [(4-methoxyphenyl)methyl] ester;

[2-(tetrahydro-3,5-1H-pyrrolizin-7a(5H)-yl)-ethyl]carbamic acid, [(3-chlorophenyl)methyl] ester.

Compounds of the present invention are prepared in accordance with the general reaction sequence illustrated below.

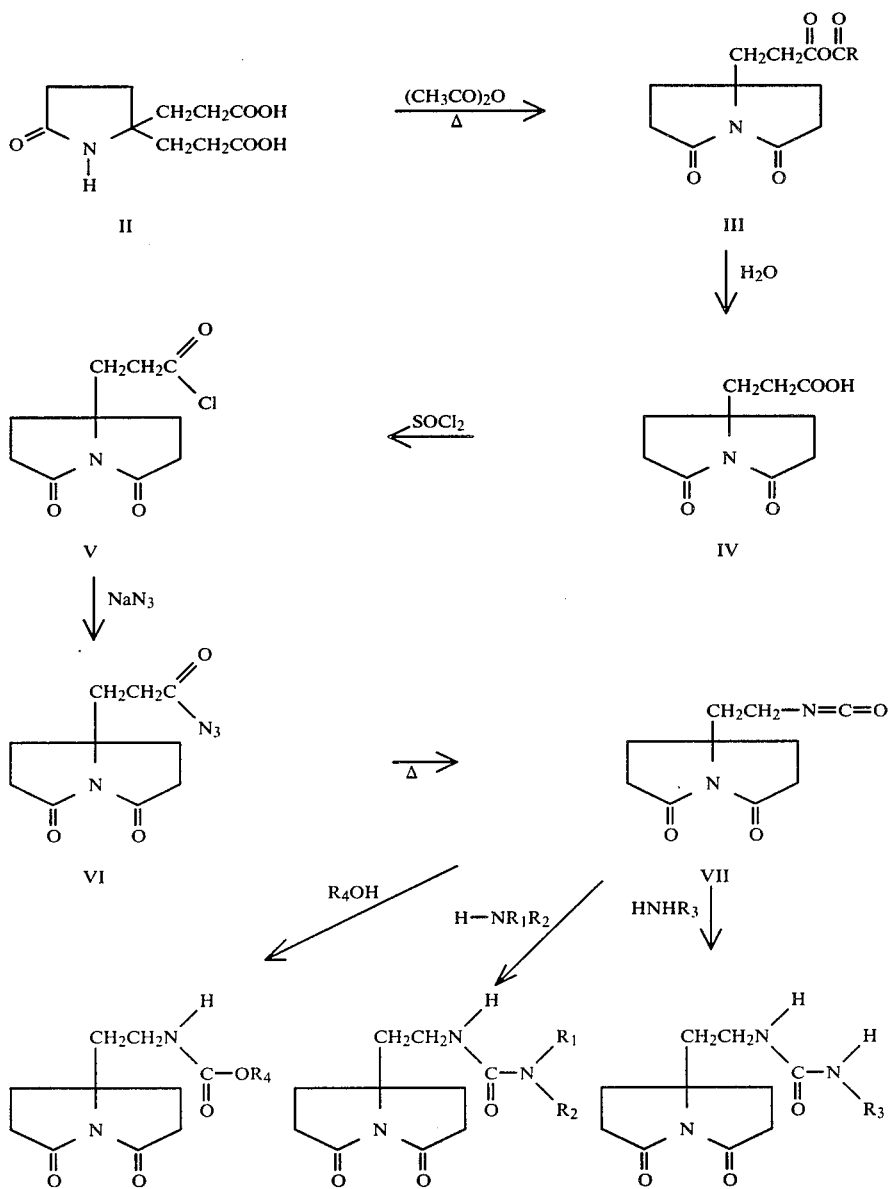

The starting material, II, is prepared by the method disclosed in U.S. Pat. No. 2,502,548.

Compound II is cyclized to compounds of formula III by heating II with a dehydrating agent such as an alkanoic acid chloride, or an aroyl acid chloride in the presence of an acid acceptor. Suitable dehydrating agents include, by way of example, acetic anhydride, propanoic anhydride, benzoyl anhydride, acetyl chloride, propionyl chloride, benzoyl chloride, and the like. Suitable acid acceptor catalysts for the reaction include tertiary amines. The preferred process for preparing compounds of formula III employs acetic anhydride in the presence of 4-dimethylaminopyridine.

Compound III is hydrolyzed by the action of water in an inert solvent to produce tetrahydro-3,5-dioxo-1H-pyrrolizine-7a(5H)-propanoic acid, IV. The acid, IV, is converted to tetrahydro-3,5-dioxo-1H-pyrrolizine-7a(5H)-propanoyl chloride, V, by conventional means as for example, with thionyl chloride.

The acid chloride, V, is converted to tetrahydro-3,5-dioxo-1H-pyrrolizine-7a(5H)-propanoyl azide, VI, by reaction of V with sodium azide in water, with the acyl azide, VI, being subsequently thermally converted to the isocyanate, VII. The isocyanate, VII, dihydro-7a(5H)-2-isocyanatoethyl)-1H-pyrrolizine-3,5(2H,6H)-dione, is believed to be a novel compound, useful as an intermediate for the preparation of compounds in accordance with the present invention.

The isocyanate, VII, is reacted by conventional reaction means with the appropriate reagent to yield the compounds of formula I. For example, reaction of the isocyanate, VII, with the desired alcohol yields a urethane of formula I where A is alkoxyl, phenoxyl, substituted phenoxyl, phenylmethoxyl, or substituted phenylmethoxyl. The lower alcohols, and substituted or unsubstituted phenols or phenylmethanols employed in the reaction with the isocyanate, VII, are known compounds.

Reaction of the isocyanate, VII, with ammonia or the desired primary or secondary amine yields a urea of formula I where A is $NH_2$, $NHR_1$, or $NR_1R_2$ where $R_1$ and $R_2$ are as previously defined. The primary or secondary amines employed in the reaction with the isocyanate, VII, to produce ureas of the present invention are known compounds.

Compounds where the group, A, is an amine such as 4-pyridyl, N,N-bis(1-methylethyl)aminoethyl, or other amine containing a basic nitrogen atom, are capable of forming pharmaceutically acceptable salts with organic and inorganic acids. Suitable acids include hydrochloric, sulfuric, phosphoric acetic, citric, oxalic, malonic, salicyclic, malic, fumaric, succinic, ascorbic, maleic, mathesulfonic, and the like.

The salts are prepared by contacting the free base form of compounds of the present invention with a sufficient amount of the desired acid in the conventional manner. The salt is isolated by filtration, evaporation or other conventional means. The free base may be regenerated, if desired, by contacting the salt with an aqueous solution of a base such as dilute sodium hydroxide, potassium carbonate, ammonia, sodium bicarbonate, and the like.

The free base form of compounds of the present invention may differ somewhat from the salt forms in such physical properties as melting point and solubility in polar solvents such as water, but the salts are otherwise equivalent to the free base forms for the purposes of this invention.

The compounds of the invention can exist in unsolvated as well as solvated forms, including hydrated forms. In general, the solvated forms, with pharmaceutically acceptable solvents such as water, ethanol, and the like are equivalent to the unsolvated forms for purposes of the invention.

The alkyl groups contemplated by the invention unless otherwise stated, comprise both straight and branched carbon chains of from one to about six carbon atoms. Representative of such groups are methyl, ethyl, isopropyl, pentyl, 3-methylpentyl, and the like.

Cycloalkyl groups contemplated by the invention are those having five or six members such as cyclopentyl and cyclohexyl which may be optionally substituted by alkyl of one to four carbon atoms but especially methyl.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solublizers, lubricants, suspending agents, binders or tablet disintegrating agents; it can also be encapsulating material. In powders, the carrier is a finely divided solid which is in admixture with the finely divided active compound. In the tablet, the active compound is mixed with a carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool, and thereby to solidify.

Liquid form preparations include solutions, suspensions, and emulsions. As an example, it may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suiable colorants, flavors, stabilizing, and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted shortly before use, to liquid form preparations for either oral or parenteral administration. Such liquid forms include solutions, suspensions, and emulsions. These particular solid form preparaions are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid from preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain in addition to the active material, flavorants, colorants, stabilizers, buffers, artificial and natural sweeteners, dispersants, thickeners, solubilizing agents, and the like. The liquid utilized for preparing the liquid from preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself, or it can be the appropriate number of any of these in packaged form.

The quantity of active compound in a unit dose of preparation may be varied or adjusted from 1 mg to 500 mg, preferably to 5 to 100 mg according to the particular application and the potency of the active ingredient.

The compositions can, if desired, also contain other compatable therapeutic agents such as 3-phenoxypyridine or N-[2-[Bis(1-methylethyl)amino]-ethyl]-2-oxo-pyrrolidineacetamide.

In therapeutic use as cognition activators, the mammalian dosage range for a 70 kg subject is from 1 to 1500 mg/kg of body weight per day or preferably 25 to 750 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The effectiveness of the aforementioned compounds was determined by the test designed to show the compound's ability to reverse amnesia produced by electroconvulsive shock. The test is fully described in U.S. Pat. No. 4,145,347, issued Mar. 20, 1979, and is herein incorporated by reference. The test compounds in the present instance were administered orally and the length of electroconvulsive shock was 1.0 second.

The following criteria are used in interpreting the percent of amnesia reversal scores: 40 percent or more (active=A), 25 to 39 percent (borderline=C), and 0 to 24 percent (inactive=N).

The table below indicates the percent amnesia reversal determined for representative examples of compounds in accordance with the present invention when administered orally to standard laboratory animals in the test referenced above.

stirred with 6.0 g (0.05 mol) of thionyl chloride at room temperature for 18 hours.

At the end of this period, the solution is concentrated under vacuum to yield tetrahydro-3,5-dioxo-1H-pyrrolizine-7a(5H)-propanoyl chloride as a white solid. The material was used in the next step without further purification.

Preparation of tetrahydro-3,5-dioxo-1H-pyrrolizine-7a(5H)-propanoyl azide.

A solution of 10.8 g (0.048 mol) of tetrahydro-3,5-dioxo-1H-pyrrolizine-7a(5H)-propanoyl chloride in 400 ml of acetone was added to 3.64 g (0.05 mol of sodium azide in 25 ml of water with stirring at 10° C. The solution was stirred for one hour and then filtered. The filtrate was concentrated in vacuum to yield tetrahydro-3,5-dioxo-1H-pyrrolizine-7a(5H)-propanoyl azide, employed in the next step without further purification.

Preparation of dihydro-7a(5H)-(2-isocyanatoethyl)-1H-pyrrolizine-3,5(2H,6H)-dione.

A solution of 4.4 g (0.047 mol) of tetrahydro-3,5-dioxo-1H-pyrrolizine-7a(5H)-propanoyl azide in 20 ml of chloroform was added dropwise to 200 ml of refluxing toluene. The resulting toluene solution of dihydro-7a(5H)-(2-isocyanatoethyl)-1-H-pyrrolizine-3,5(2H,6H)-dione was employed as such in subsequent steps without further purification of the material.

Preparation of N-[2-(tetrahydro-3,5-dioxo-1H-pyrrolin-7a(5H)-ylethyl]urea

A solution of 4.9 g (0.0235 mol) of dihydro-7a(5H(3-isocyanatoethyl)-1H-pyrrolizine-3,5(2H,6H)-dione in

TABLE

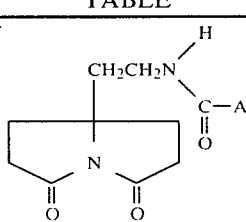

| Compound | A | Dose (mg/kg of body weight) | | | | | |
|---|---|---|---|---|---|---|---|
| | | 100 | 80 | 20 | 10 | 5 | 1 |
| 1 | —NH₂* | | 31(C) 10(N) | 50(A) 36(C) | | 62(A) 20(N) | |
| 2 | —NHCH₂—φ | 46(A) | | | 30(C) | | 0(N) |
| 3 | —OCH₂—φ | 56(A) | (N) | 47(A) | | | 62(A) |

*Two replications, 20 mg and 5 mg/kg would still have A ratings if the results were averaged. This is within the experimental limits of the test system.

The following preparative examples are provided to enable one skilled in the art to practice the present invention. The examples are merely illustrative of the present invention and should not be viewed as limiting its scope as defind by the appended claims.

EXAMPLE 1

Preparation of tetrahydro-3,5-dioxo-1H-pyrrolizine-7(5H)-propanoyl chloride.

A suspension of tetrahydro-3,5dioxo-1H-pyrrolizine-7a-(5H-propanoic acid (10.0 g, 0.047 mol) in 500 ml of methylene chloride containing 0.3 ml of pyridine, is 100 ml of toluene was saturated with gaseous ammonia. The solid which formed was collected by filtration to yield N-[2-tetrahydro-3,5-dioxo-1H-pyrrolizin-7a(5H)-yl)ethyl]urea, mp 180°–182° C.

EXAMPLE 2

Preparation of [2-(Tetrahydro-3,5-dioxo-1H-pyrrolizin-7a(5H)-yl)ethyl]carbamic acid phenylmethyl ester A solution of 4.9 (0.0235 mol) of dihydro-7a(5H)-(3-isocyanatoethyl)-1H-pyrrolizine-3,5(2H,6H)-dione in 100 ml of toluene was treated with a solution of 2.56 g (0.024 mol) of phenylmethanol in 10 ml of toluene. The resulting mixture was heated under reflux for two hours, after which time the solution was concentrated under vacuum to yield [2-(tetrahydro-3,5-dioxo-1H-pyrrolizine-7a(5H)-yl)ethyl]carbamic acid phenylmethyl ester, mp 118°–120° C.

EXAMPLE 3

Preparation of N-(phenylmethyl)-N'-[2-(tetrahydro-3,5-1H-pyrrolizin-7a(5H)-yl)ethyl]urea A solution of 4.9 g (0.0235 mol) of dihydro-7a(5H)-(3-isocyanatoethyl)-1H-pyrrolizine-3,5(2H,6H)-dione in 100 ml of toluene was treated with a solution of 2.56 g (0.024 mol) of phenylmethylamine in 10 ml of toluene. The mixture was stirred at room temperature for two hours after which time the solid which separated was collected by filtration to yield N-(phenylmethyl)-N'-[2-(tetrahydro-3,5-1H-pyrrolizin-7a(5H)-yl)ethyl]urea, mp 145°–147° C.

We claim:

1. A compound having the formula

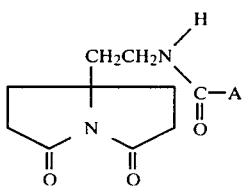

wherein A is NR₁R₂ where R₁ and R₂ are independently hydrogen, lower alkyl, or lower alkylene; wherein A is NHR₃ where R₃ is phenyl, phenylmethyl, N,N-bis(1-methylethyl)-aminoethyl or 4-pyridyl; or wherein A is —OR₄ where R₄ is lower alkyl, phenyl, phenylmethyl, or phenyl or phenylmethyl substituted in the 2-, 3-, or 4-position with chlorine, fluorine, lower alkoxy, or phenylmethoxy.

2. A compound in accordance with claim 1 wherein A is NR₁R₂ where R₁ and R₂ are independently hydrogen, lower alkyl, lower allkylene.

3. A compound in accordance with claim 1 wherein A is NHR₃ where R₃ is phenyl or phenylmethyl.

4. A compound in accordance with claim 1 wherein A is NHR₃ where R₃ is N,N-bis(1-methylethyl)-aminoethyl or 4-pyridyl.

5. A compound in accodance with claim 1 wherein A is —OR₄ where R₄ is lower alkyl.

6. A compound in accordance with claim 1 wherein A is —OR₄ where R₄ is phenyl or phenyl substituted in the 2-, 3-, or 4-position with chlorine, fluorine, methoxy, or phenylmethoxy.

7. A compound in accordance with claim 1 wherein A is —OR₄ where R₄ is phenylmethyl or phenylmethyl substituted in the 2-, 3-, or 4-position with chlorine, fluorine, methoxy, or phenylmethoxy.

8. A compound in accordance with claim 2 being N-[2-(tetrahydro-3,5-dioxo-1H-pyrrolizin-7a(5H)-yl)ethyl]urea.

9. A compound in accordance with claim 2 being N-methyl-N'-[2-(tetrahydro-3,5-dioxo-1H-pyrrolizin-7a(5H)-yl)ethyl]urea.

10. A compound in accordance with claim 2 being N-2-propenyl-N'-[2-tetrahydro-3,5-dioxo-1H-pyrrolizin-7a(5H)-yl)ethyl]urea.

11. A compound in accordance with claim 2 being N,N-dimethyl-N'-[2-(tetrahydro-3,5-dioxo-1H-pyrrolizin-7a(5H)-yl)ethyl]urea.

12. A compound in accordance with claim 2 being N,N-diethyl-N'-[2-(tetrahydro-3,5-dioxo-1H-pyrrolizin-7a(5H)-yl)ethyl]urea.

13. A compound in accordance with claim 3 being N-phenyl-N'-[2-tetrahydro-3,5-dioxo-1H-pyrrolizin-7a(5H)-yl)ethyl]urea.

14. A compound in accordance with claim 3 being N-(phenylmethyl)-N'-[2-(tetrahydro-3,5-dioxo-1H-pyrrolizin-7a(5H)-yl)ethyl]urea.

15. A compound in accordance with claim 4 being N-[2-[bis(1-methylethyl)amino[ethyl]-N'-[2-(tetrahydro-3,5-dioxo-1H-pyrrolizin-7a(5H)-yl)ethyl]urea.

16. A compound in accordance with claim 4 being N-4-pyridyl-N'-[2-tetrahydro-3,5-dioxo-1H-pyrrolizin-7a(5H)-yl)ethyl]urea.

17. A compound in accordance with claim 5 being [2-tetrahydro-3,5-dioxo-1H-pyrrolizin-7a(5H)-yl)ethyl]-carbamic acid, methyl ester.

18. A compound in accordance with claim 5 being [2-(tetrahydro-3,5-dioxo-1H-pyrrolizin-7a(5H)-ylethyl]-carbamic acid, ethyl ester.

19. A compound in accordance with claim 6 being [2-(tetrahydro-3,5-dioxo-1H-pyrrolizin-7a(5H)-yl)ethyl]carbamic acid, phenyl ester.

20. A compound in accordance with claim 6 being [2-(tetrahydro-3,5-dioxo-1H-pyrrolizin-7a(5H)-yl-ethyl]carbamic acid, 4-fluorophenylester.

21. A compound in accordance with claim 6 being [2-(tetrahydro-3,5-dioxo-1H-pyrrolizin-7a(5H)-ylethyl]-carbamic acid, 2-chlorophenylester.

22. A compound in accordance with claim 6 being [2-(tetrahydro-3,5-dioxo-1H-pyrrolizin-7a(5H)-yl)ethyl]carbamic acid, 4-methoxyphenylester.

23. A compound in accordance with claim 7 being [2-tetrahydro-3,5-dioxo-1H-pyrrolizin-7a(5H)-yl)ethyl]-carbamic acid, phenymethyl ester.

24. A compound in accordance with claim 7 being [2-(tetrahydro-3,5-dioxo-1H-pyrrolizin-7a(5H)-yl)ethyl]carbamic acid, [(4-methoxyphenyl)methyl] ester.

25. A compound in accodance with claim 7 being [2-(tetrahydro-3,5-dioxo-1H-pyrrolizin-7a(5H)-yl)ethyl]carbamic acid, [(3-chlorophenyl)methyl] ester.

26. An intermediate, useful in the preparation of compounds of formula I of claim 1, said intermediate being dihydro-7a(5H)-(2-isocyanatoethyl)-1H-pyrrolizin-3,5(2H,6H)-dione.

27. A pharmaceutical composition for reversing the effects of electroconvulsive shock induced amnesia comprising an amnesia-reversing effective amount of a compound having the structural formula

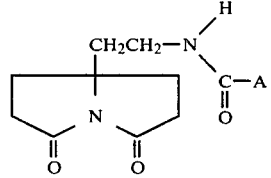

wherein A is NR₁R₂ where R₁ and R₂ are independently hydrogen, lower alkyl, or lower alkylene; wherein A is NHR₃ where R₃ is phenyl, phenylmethyl, N,N-bis(1-methylethyl)aminoethyl or 4-pyridyl; or wherein A is —OR₄ where R₄ is lower alkyl, phenyl, phenylmethyl, or phenyl or phenylmethyl substituted in the 2-, 3-, or 4-position with chlorine, fluorine, hydroxy, methoxy, or phenylmethoxy in combination with a pharmaceutically acceptable carrier.

28. A method of reversing the effects of electroconvulsive shock-induced amnesia in a mammal which comprises administering to said mammal in need of such treatment the pharmaceutical composition in accordance with claim 27.

* * * * *